(12) United States Patent
Sillers et al.

(10) Patent No.: US 6,322,590 B1
(45) Date of Patent: Nov. 27, 2001

(54) INTERNAL NASAL IMPLANT

(76) Inventors: Michael J. Sillers, 423 Heatherwood Forest Cir., Hoover, AL (US) 35244; J. Todd Strong, 3414 Heather La., Birmingham, AL (US) 35216; Timothy E. Taylor, 4780 Sandpiper La., Hoover, AL (US) 35244

( * ) Notice: Subject to any disclaimer, the term of this patent is extended or adjusted under 35 U.S.C. 154(b) by 0 days.

(21) Appl. No.: 09/436,710

(22) Filed: Nov. 9, 1999

(51) Int. Cl.[7] .............................. A61F 2/18; A61M 29/00
(52) U.S. Cl. ............................................. 623/10; 606/199
(58) Field of Search .............................. 623/10; 606/199, 606/204.45

(56) References Cited

U.S. PATENT DOCUMENTS

| | | | |
|---|---|---|---|
| 5,041,138 | * 8/1991 | Vacanti et al. | 623/16.11 |
| 5,133,754 | * 7/1992 | Laghi | 623/11.11 |
| 5,664,567 | * 9/1997 | Linder | 128/207.18 |
| 6,024,918 | * 2/2000 | Hendriks et al. | 422/44 |
| 6,065,470 | * 5/2000 | Van Cromvoirt et al. | 128/200.24 |
| 6,098,616 | * 8/2000 | Lundy, Jr. et al. | 128/200.24 |
| 6,106,541 | * 8/2000 | Hurbis | 606/199 |

* cited by examiner

Primary Examiner—David H. Willse
Assistant Examiner—Suzette J. Jackson
(74) Attorney, Agent, or Firm—Tarolli, Sundheim, Covell, Tummino & Szabo L.L.P.

(57) ABSTRACT

An internal nasal implant (10) for opening nasal valves (12, 13) of a human nasal cavity (14) includes an elongate body (16) of biocompatible material having a length to span dorsal surface portions of first and second upper lateral cartilage of a human nose. The elongate body (16) has a first end portion (22) and a second end portion (26) connected by a base portion to form an overall V-shape. The first end portion (22) and the second end portion (26) are capable of biasing the first and second upper lateral cartilage apart to increase air flow through the nasal valves (12, 13).

9 Claims, 1 Drawing Sheet

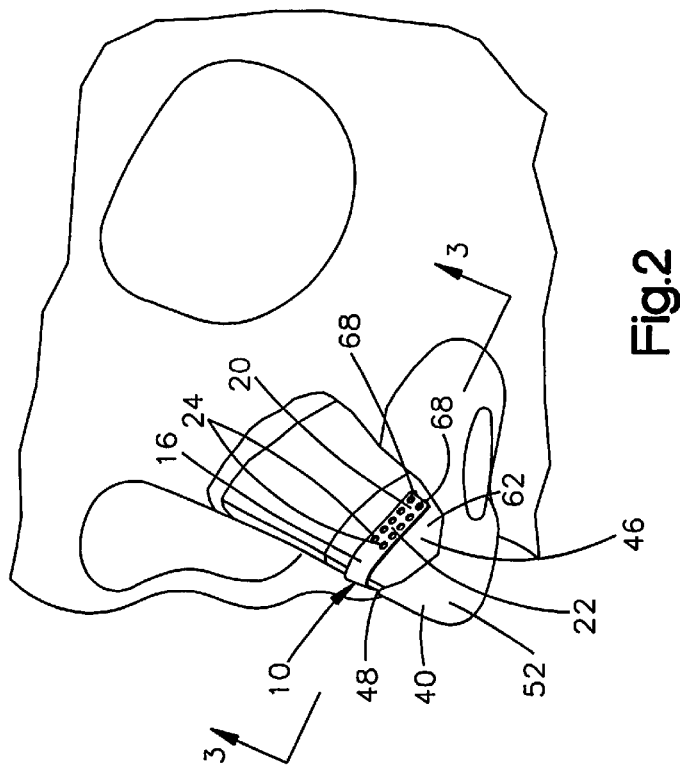
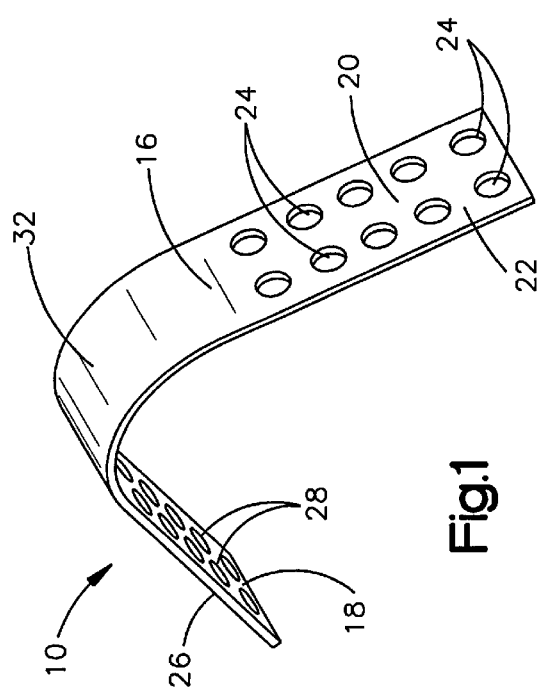
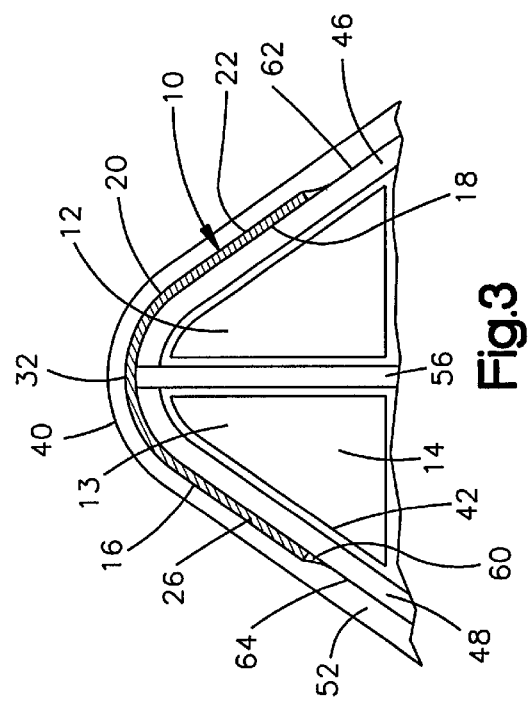

INTERNAL NASAL IMPLANT

FIELD OF THE INVENTION

The present invention relates to an internal nasal implant for opening a nasal valve of a human nasal cavity

BACKGROUND OF THE INVENTION

The narrowest area in the nasal cavity is referred to as the nasal valve. The nasal valve is located at the junction of the upper and lower lateral cartilage and includes the nasal septum. The upper lateral cartilage on each side of the nasal cavity is the only portion of the nasal valve that collapses during inspiration of air. The nasal cavity accounts for 50–60% of total airway resistance. Numerous non-implantable products and surgical procedures are available to increase the area of the nasal valve and to decrease nasal airflow resistance.

SUMMARY OF THE INVENTION

The present invention is an internal nasal implant for opening nasal valves of a human nasal cavity. The nasal implant includes an elongate body of biocompatible material having a length to span dorsal surface portions of first and second upper lateral cartilage of a human nose. The elongate body has a first end portion and a second end portion connected by a base portion to form an overall V-shape. The first end portion and the second end portion are capable of biasing the first and second upper lateral cartilage apart to increase airflow through the nasal valves.

BRIEF DESCRIPTION OF THE DRAWINGS

The foregoing and other features of the present invention will become apparent to one skilled in the art to which the present invention relates upon consideration of the following description of the invention with reference to the accompanying drawings wherein:

FIG. 1 is a pictorial view of a nasal implant;

FIG. 2 is a pictorial view of a human nose with the nasal implant of FIG. 1 implanted; and FIG. 3 is a view taken along the line 3—3 of FIG. 2 showing the nasal implant in the nose.

DESCRIPTION OF A PREFERRED EMBODIMENT

A nasal implant 10 for opening nasal valves 12 and 13 of a human nasal cavity 14 is shown in FIGS. 1–3. The implant 10 includes an elongate body 16 made of a biocompatible material. The elongate body 16 (FIG. 1) has a first surface 18 and an opposite second surface 20. The first and second surfaces 18 and 20 extend parallel to each other.

The elongate body 16 has a first end portion 22. The first end portion 22 is perforated or has openings 24 for receiving suture material and/or ingrowth of body tissue. The elongate body 16 has a second opposite end portion 26. The second end portion 26 is perforated or has openings 28 for receiving suture material and/or ingrowth of body tissue.

A base portion 32 (FIG. 1) of the elongate body 16 interconnects the first and second end portions 22 and 26. The end portions 22 and 26 extend from the base portion 32 so that the implant 10 has a V-shape.

The implant 10 is made of a biocompatible material that has elastic properties in order to maintain the shape of the implant when external forces are applied. Preferably, the biocompatible material is metallic. Furthermore, the metallic material is preferably a nickel-titanium alloy, such as nitinol. Alternatively, the biocompatible material may be a polymer, such as silicone.

The implant 10 (FIGS. 2 and 3) is implanted into a nose 40 of a patient. An incision is made through intranasal skin 42 caudal to lower margins of first and second upper lateral cartilage 46 and 48. Through this incision, soft tissue 52 is elevated off dorsal surface portions 62 and 64 of the first and second upper lateral cartilage 46 and 48 and the dorsal nasal septum 56 to create a pocket 60 (FIG. 3) for receiving the implant 10.

The implant 10 is placed into the pocket 60 with the surface 18 engaging the dorsal surface portions 62 and 64 of the first and second upper lateral cartilage 46 and 48. The surface 20 faces away from the dorsal surface portions 62 and 64 of the cartilage 46 and 48. The end portion 22 (FIG. 2) of the implant 10 is suture fixated to the dorsal surface portion 62 of the first lateral cartilage 46 with suture material 68 extending through openings 24. The end portion 26 of the implant 10 is suture fixated to the dorsal surface portion 64 of the upper lateral cartilage 48 with suture material (not shown) extending through openings 28. The incision is then closed with suture material.

The first and second upper lateral cartilage 46 and 48 are preferably suture fixated to the first and second end portions 22 and 26 with a biodegradable suturing material. Alternatively, the first and second upper lateral cartilage 46 and 48 may be suture fixated to the first and second end portions 22 and 26 with a non-biodegradable suturing material. Also, the incision is closed with a biodegradable suturing material.

When the implant 10 is implanted in the nose 40, tissue may grow into the openings 24 and 28 to secure the implant in the nose. The first and second end portions 22 and 26 of the implant 10 are capable of biasing the first and second upper lateral cartilage 46 and 48 apart, as viewed in FIG. 3, to increase airflow through the nasal valves 12 and 13. The implant 10 reduces the tendency of the nasal valves 12 and 13 to collapse during inspiration of air.

From the above description of the invention, those skilled in the art will perceive improvements, changes and modifications. Such improvements, changes and modifications within the skill of the art are intended to be covered by the appended claims.

Having described the invention, the following is claimed:

1. An internal nasal implant for opening nasal valves of a human nasal cavity comprising:

an elongate body of biocompatible material having a length to span dorsal surface portions of first and second upper lateral cartilage of a human nose;

said elongate body having a first end portion and a second end portion connected by a base portion to form an overall V-shape;

said first end portion and said second end portion being capable of biasing the first and second upper lateral cartilage apart to increase airflow through the nasal valves; and said first end portion and said second end portion possessing holes for insertion of suture material to secure said nasal implant to body tissue.

2. The nasal implant as defined in claim 1 wherein said biocompatible material is metallic.

3. Th e nasal implant as defined i n claim 2 wherein said biocompatible material is Nitinol.

4. The nasal implant as defined in claim 1 wherein said biocompatible material is a polymer.

5. The nasal implant as defined in claim 4 wherein said biocompatible material is silicone.

6. The nasal implant as defined in claim 1 wherein said elongate body is perforated to allow ingrowth of body tissue and insertion of suture material to secure said implant to body tissue.

7. An internal nasal implant for opening nasal valves of a human nasal cavity comprising:
- an elongate body of biocompatible material having a length to span dorsal surface portions of first and second upper lateral cartilage of a human nose;
- said elongate body having a first end portion and a second end portion connected by a base portion to form an overall V-shape;
- said first end portion and said second end portion being capable of biasing the first and second upper lateral cartilage apart to increase airflow through the nasal valves;
- said elongate body being perforated to allow ingrowth of body tissue and insertion of suture material to secure said implant to body tissue.

8. An internal nasal implant for opening the nasal valves of a human nasal cavity comprising:
- a first surface engageable with first and second upper lateral cartilage;
- a second surface opposite said first surface for facing away from the first and second upper lateral cartilage;
- a first end portion connectable with the first upper lateral cartilage;
- a second end portion connectable with the second upper lateral cartilage, said first and second end portions being biased away from each other to increase airflow through the nasal valves when said nasal implant is connected with the first and second upper lateral cartilage;
- a base portion interconnecting said first and second end portions; and
- openings extending from said first surface to said second surface for receiving suturing material to connect said nasal implant to the first and second upper lateral cartilage.

9. An internal nasal implant for opening the nasal valves of a human nasal cavity comprising:
- a first surface engageable with first and second upper lateral cartilage;
- a second surface opposite said first surface for facing away from the first and second upper lateral cartilage;
- a first end portion connectable with the first upper lateral cartilage;
- a second end portion connectable with the second upper lateral cartilage, said first and second end portions being biased away from each other to increase airflow through the nasal valves when said nasal implant is connected with the first and second upper lateral cartilage;
- a base portion interconnecting said first and second end portions; and
- openings extending from said first surface to said second surface for ingrowth of body tissue.

* * * * *